United States Patent
Morsi

(10) Patent No.: US 11,284,911 B2
(45) Date of Patent: Mar. 29, 2022

(54) CENTRAL CLOT STABILIZER AND MANIPULATOR

(71) Applicant: NOHA, LLC, Houston, TX (US)

(72) Inventor: Hesham Morsi, Houston, TX (US)

(73) Assignee: Hesham Morsi, Houston, TX (US)

(*) Notice: Subject to any disclaimer, the term of this patent is extended or adjusted under 35 U.S.C. 154(b) by 196 days.

(21) Appl. No.: 16/319,231

(22) PCT Filed: Jul. 21, 2017

(86) PCT No.: PCT/US2017/043282
§ 371 (c)(1),
(2) Date: Jan. 18, 2019

(87) PCT Pub. No.: WO2018/017952
PCT Pub. Date: Jan. 25, 2018

(65) Prior Publication Data
US 2019/0269424 A1    Sep. 5, 2019

Related U.S. Application Data

(60) Provisional application No. 62/365,472, filed on Jul. 22, 2016.

(51) Int. Cl.
*A61B 17/221* (2006.01)
*A61M 25/09* (2006.01)
(Continued)

(52) U.S. Cl.
CPC ............ *A61B 17/221* (2013.01); *A61F 2/01* (2013.01); *A61F 2/012* (2020.05); *A61M 25/09* (2013.01);
(Continued)

(58) Field of Classification Search
CPC ............ A61B 17/221; A61B 17/32056; A61B 2017/22034; A61B 17/22031;
(Continued)

(56) References Cited

U.S. PATENT DOCUMENTS

| 6,066,149 A | 5/2000 | Samson et al. |
| 6,530,935 B2 | 3/2003 | Wensel et al. |

(Continued)

FOREIGN PATENT DOCUMENTS

| WO | 2002/094111 A2 | 11/2002 |
| WO | 2011/119872 A1 | 9/2011 |

OTHER PUBLICATIONS

International Preliminary Report on Patentability issued in corresponding International Application No. PCT/US2017/043282 dated Jan. 31, 2019.

*Primary Examiner* — Elizabeth Houston
*Assistant Examiner* — Michael G Mendoza
(74) *Attorney, Agent, or Firm* — Norton Rose Fulbright US LLP

(57) ABSTRACT

A clot encasement and removal device for removing a vascular obstruction is disclosed. The encasement device comprises proximal and distal capture members and a central stabilizer. The central stabilizer provides several points of contact for interacting with and manipulating an intravascular obstruction. The central stabilizer may be coupled to the distal capture member, allowing the central stabilizer and distal capture member to be manipulated in unison. The central stabilizer may reside on a distinct delivery wire, enabling independent control of proximal and distal capture members and the central stabilizer. The proximal capture member may comprise a furrowed delivery wire to enable retraction of at least a portion of the central stabilizer within the proximal capture member.

23 Claims, 7 Drawing Sheets

(51) Int. Cl.
*A61M 29/02* (2006.01)
*A61F 2/01* (2006.01)
*A61B 17/22* (2006.01)

(52) U.S. Cl.
CPC ... *A61M 29/02* (2013.01); *A61B 2017/22034* (2013.01)

(58) Field of Classification Search
CPC ..... A61B 17/22032; A61B 2017/22035; A61F 2/01; A61F 2/0105; A61F 2/011; A61F 2/012; A61F 2/013; A61F 2002/016; A61F 2002/018; A61F 2/0103; A61F 2/014; A61F 2/0108; A61F 2002/015; A61M 25/09; A61M 29/02
See application file for complete search history.

(56) References Cited

U.S. PATENT DOCUMENTS

| | | | |
|---|---|---|---|
| 8,343,167 | B2 | 1/2013 | Henson |
| 8,475,488 | B2 | 7/2013 | Cartier et al. |
| 8,608,754 | B2 | 12/2013 | Wensel et al. |
| 8,900,265 | B1 | 12/2014 | Ulm, III |
| 9,301,769 | B2 | 4/2016 | Brady et al. |
| 9,351,749 | B2 | 5/2016 | Brady et al. |
| 2009/0105653 | A1 | 4/2009 | Spenser et al. |
| 2009/0326575 | A1* | 12/2009 | Galdonik .......... A61B 17/12109 606/200 |
| 2011/0152920 | A1 | 6/2011 | Eckhouse et al. |
| 2011/0282379 | A1* | 11/2011 | Lee .......... A61F 2/014 606/200 |
| 2012/0059356 | A1 | 3/2012 | di Palma et al. |
| 2012/0172915 | A1* | 7/2012 | Fifer .......... A61F 2/012 606/200 |
| 2012/0289996 | A1* | 11/2012 | Lee .......... A61F 2/013 606/200 |
| 2013/0053882 | A1* | 2/2013 | Hocking .......... A61B 17/221 606/200 |
| 2013/0144326 | A1 | 6/2013 | Brady et al. |
| 2013/0190789 | A1 | 7/2013 | McGuckin, Jr. et al. |
| 2013/0197567 | A1* | 8/2013 | Brady .......... A61B 17/221 606/200 |
| 2013/0310803 | A1* | 11/2013 | Morsi .......... A61B 17/22032 604/508 |
| 2014/0100597 | A1* | 4/2014 | Wang .......... A61F 2/012 606/200 |
| 2014/0243885 | A1 | 8/2014 | Eckhouse et al. |
| 2015/0250497 | A1 | 9/2015 | Marks et al. |
| 2015/0374393 | A1 | 12/2015 | Brady et al. |
| 2016/0022296 | A1 | 1/2016 | Brady et al. |
| 2018/0235742 | A1* | 8/2018 | Fields .......... A61F 2/0105 |
| 2018/0311029 | A1* | 11/2018 | Hocking .......... A61F 2/012 |

* cited by examiner

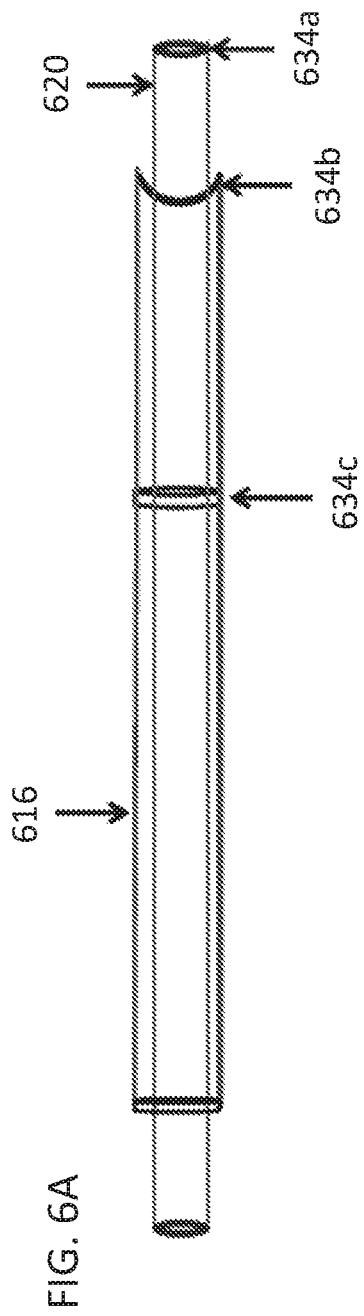
FIG. 6A
FIG. 6B
FIG. 6C

CENTRAL CLOT STABILIZER AND MANIPULATOR

CROSS REFERENCE TO RELATED APPLICATIONS

This application is a national phase application under 35 U.S.C. § 371 that claims priority to International Application No. PCT/US2017/043282 filed Jul. 22, 2017, which claims priority to U.S. Provisional Application No. 62/365,472 filed Jul. 22, 2016, all of which are incorporated herein by reference in their entirety.

TECHNICAL FIELD

Embodiments of the present disclosure relate generally to medical devices and methods of using same, and more specifically, to medical devices for treating, including treating an occluded biological lumen, such as an embolus or clot in a blood vessel.

BACKGROUND

This section is intended to introduce various aspects of the art, which may be associated with exemplary embodiments of the present disclosure. This discussion is believed to assist in providing a framework to facilitate a better understanding of particular aspects of the present disclosure. Accordingly, it should be understood that this section should be read in this light, and not necessarily as any admission of prior art.

There are many reasons a blood vessel becomes blocked or obstructed. One way is from deposition of thrombus on the walls of the blood vessels. The buildup of these clots can restrict blood flow. Because arterial blockages reduce blood flow through the affected vessel, any blockage or obstruction can lead to many serious medical complications. For instance, tissue relying on the blood's supply of oxygen may become damaged due to the decrease in the oxygen amount or the blockage can result in a heart attack if the obstructed vessel supplies blood to the heart itself.

While various methods are available to treat a blockage or obstruction through removal of the obstruction, these methods do not sufficiently capture and retain the particulate matters from the obstruction to prevent them from migrating to another area of the vascular system where they can get lodged again.

The present disclosure provides solutions to long-felt needs in the art to treat occluded vessels.

SUMMARY

The foregoing has outlined rather broadly the features and technical advantages of the embodiments of the present disclosure in order that the detailed description of these embodiments that follows may be better understood. Additional features and advantages of the embodiments of the present disclosure will be described hereinafter which form the subject of the claims of the present disclosure. It should be appreciated by those skilled in the art that the conception and specific embodiment disclosed may be readily utilized as a basis for modifying or designing other structures for carrying out the same purposes of the present disclosure. It should also be realized by those skilled in the art that such equivalent constructions do not depart from the spirit and scope of the present disclosure as set forth in the appended claims. The novel features which are believed to be characteristic of the present disclosure, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

The term "coupled" is defined as connected, although not necessarily directly, and not necessarily mechanically. The terms "a" and "an" are defined as one or more unless this disclosure explicitly requires otherwise. The term "substantially" is defined as being largely but not necessarily wholly what is specified (and include wholly what is specified) as understood by one of ordinary skill in the art. In any disclosed embodiment, the term "substantially" may be substituted with "within [a percentage] of" what is specified, where the percentage includes 0.1, 1, 5, and 10 percent. The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, an encasement sleeve that "comprises," "has," "includes" or "contains" one or more elements possesses those one or more elements, but is not limited to possessing only those one or more elements. Likewise, an element of a system or composition that "comprises," "has," "includes" or "contains" one or more features possesses those one or more features, but is not limited to possessing only those one or more features. Furthermore, a structure or composition that is configured in a certain way is configured in at least that way, but may also be configured in ways that are not listed. Metric units may be derived from the English units provided by applying a conversion and rounding to the nearest millimeter. The feature or features of one embodiment may be applied to other embodiments, even though not described or illustrated, unless expressly prohibited by this disclosure or the nature of the embodiments. Any embodiment of any of the disclosed container assemblies and compositions can consist of or consist essentially of—rather than comprise/include/contain/have—any of the described elements and/or features and/or steps. Thus, in any of the claims, the term "consisting of" or "consisting essentially of" can be substituted for any of the open-ended linking verbs recited above, in order to change the scope of a given claim from what it would otherwise be using the open-ended linking verb. Details associated with the embodiments described above and others are presented below.

Embodiments of the disclosure are directed towards a clot encasement and removal device. In particular embodiments, the device comprises proximal and distal capture members within which a clot or other obstruction may be sequestered. In specific aspects, the device further comprises a central stabilizer for direct contact, stabilization, and manipulation of a vascular obstruction. The central stabilizer may be used at least in part to effectively grab an obstruction. The central stabilizer may be operated in unison with the proximal capture member, or it may be independently operated. In some embodiments, the proximal capture member features a furrowed section for allowing at least a portion of the central stabilizer to be withdrawn into the proximal capture member.

The clot encasement device is configured to offer a multitude of options for capturing and manipulating obstructions. Upon making contact and stabilizing an obstruction, the central stabilizer may be pulled into the proximal capture member, the stabilizer may be pushed into the distal capture member, or either or both of the capture members may be directed to encase at least a portion of the central stabilizer. The central stabilizer may hold an obstruction in place, and the proximal and/or distal capture members may be manipulated to encase the obstruction. Both proximal and distal capture members may come together to provide an encasing volume for the obstruction. The proximal and distal capture members may comprise frame components at open ends with the same or different diameters. The diameters may be selected such that one frame fits within the other frame, at least in part. In this fashion, the proximal and distal capture members can provide a tight seal around an obstruction, thereby preventing obstruction outflow or escape.

In some embodiments, a device for removal of an obstruction in a lumen comprises a proximal capture member and a distal capture member. In specific embodiments, the proximal capture member comprises a proximal encasement sleeve and a hollow proximal delivery wire, and the distal capture member comprises a distal encasement sleeve and a discontinuous delivery wire. In some embodiments, the a central stabilizer is included and bisects the discontinuous delivery wire into proximal and distal segments.

The shape of the central stabilizer is different from the shape of the delivery wire to which it is coupled. In some embodiments, a cross-sectional shape of at least a portion of the central stabilizer is different from a cross-sectional shape of the distal segment of the discontinuous delivery wire. In some aspects, at least a portion of the proximal segment of the discontinuous delivery wire lies within the hollow proximal delivery wire.

In some embodiments, each of the proximal and distal capture members further comprises an open end and a tapered end, and a frame component coupled to a encasement sleeve. The encasement sleeve extends between the open end and tapered end. The proximal frame component, distal frame component, and/or central stabilizer may comprise a self-expanding material. In some embodiments, the proximal frame component, distal frame component, and/or central stabilizer have a collapsed configuration and an expanded configuration. The device may further comprises a catheter, within which the proximal frame component, distal frame component, and central stabilizer reside in the respective collapsed configurations.

In some aspects, at least one of the distal or proximal capture members comprises a support arm. The support arm may be coupled to the respective delivery wire and the respective frame component. The proximal or distal capture members may further comprise a fastening component slidably coupled to the respective delivery wire, thereby allowing a coupling angle of the respective frame component to be adjusted.

In some aspects, the encasement sleeves comprise a woven material of at least one of the following: a polymer, a metal, and any combination thereof. In some embodiments, the encasement sleeves are devoid of any fenestrations. The encasement sleeves may be made of a soft and flexible material. In some aspects, the encasement sleeves comprise a self-expanding material configured to bias the encasement sleeve into an expanded configuration. In some aspects, each encasement sleeve is configured to cover at least a portion of a surface of the frame component to which it is coupled. In some aspects, at least one of the proximal frame component, the distal frame component, or the central stabilizer may be configured to deliver a therapeutic substance to said obstruction.

The clot encasement device may comprise at least one radiopaque marker. In some aspects, each delivery wire comprises at least one radiopaque marker. In further aspects, each delivery wire comprises at least two radiopaque markers.

The clot encasement device may be configured to allow the central stabilizer to be withdrawn into the proximal capture member. In some aspects, at least a portion of the proximal hollow delivery wire comprises a furrowed semi-cylinder that allows at least a portion the central stabilizer to be withdrawn into the proximal encasement sleeve. In some embodiments, the furrowed semi-cylinder comprises a length that is equal to or greater than a central stabilizer length to allow the entire length of the central stabilizer to reside within the proximal encasement sleeve. In some embodiments, a proximal frame component diameter is different from a distal frame component diameter, thereby allowing one frame component to fit within the other frame component.

Some aspects of the disclosure are directed towards a clot encasement device comprising, a proximal capture member coupled to a proximal delivery wire, a distal capture member coupled to a distal delivery wire, and a central stabilizer coupled to a central delivery wire that is distinct from the distal delivery wire, thereby allowing independent manipulation of the proximal and distal capture members and the central stabilizer. In some aspects, each of the proximal and distal capture members further comprises an open end and a tapered end, a frame component coupled to a encasement sleeve, with the encasement sleeve extending between the open and tapered ends. In some embodiments, the proximal frame component, distal frame component, and/or central stabilizer comprise a self-expanding material configured to have a collapsed configuration and an expanded configuration. The device comprises a catheter, within which the proximal frame component, distal frame component, and central stabilizer reside in their respective collapsed configurations.

In some embodiments, at least a portion of the central stabilizer comprises a cross-sectional shape that is different from a cross-sectional shape of the central delivery wire. In some embodiments, the central delivery wire and the distal delivery wire lie adjacent to each other within the hollow proximal delivery wire. In other embodiments, the central delivery wire and distal delivery wire are oriented concentrically within the hollow proximal tube. In some embodiments, at least a portion of the central delivery wire resides within at least a portion of the distal delivery wire. In some aspects, at least a portion of the hollow proximal delivery wire or the distal delivery wire comprises a furrowed semi-cylinder that allows at least a portion the central stabilizer to be maneuvered into the respective encasement sleeve. In some embodiments, the furrowed semi-cylinder length is equal to or greater than the length of central stabilizer, enabling the entire length of the central stabilizer to be maneuvered into the proximal or distal encasement sleeve.

In some embodiments of the clot encasement device, at least one capture member is coupled to a support arm. The support arm may be coupled to the respective delivery wire and the respective frame component. At least one capture member may further comprise a fastening component slidably coupled to the respective delivery wire, thereby allowing a coupling angle of the respective frame component to be adjusted.

In some aspects, the encasement sleeves comprise a woven material of at least one of the following: a polymer, a metal, and any combination thereof. In some embodiments, the encasement sleeves are devoid of any fenestrations. The encasement sleeves may be made of a soft and flexible material. In some aspects, the encasement sleeves comprise a self-expanding material configured to bias the encasement sleeve into an expanded configuration. In some aspects, each encasement sleeve is configured to cover at least a portion of a surface of the frame component to which it is coupled. In some aspects, at least one of the proximal frame component, the distal frame component, or the central stabilizer may be configured to deliver a therapeutic substance to said obstruction.

The clot encasement device may comprise at least one radiopaque marker. In some aspects, each delivery wire comprises at least one radiopaque marker. In further aspects, each delivery wire comprises at least two radiopaque markers.

BRIEF DESCRIPTION OF THE DRAWINGS

The following drawings illustrate by way of example and not limitation. For the sake of brevity and clarity, every feature of a given structure may not be labeled in every figure in which that structure appears.

FIGS. 6A-6C depict three views of a proximal hollow delivery wire with a furrowed semi-cylinder. FIG. 6A is a top view of the distal delivery wire residing within the hollow proximal delivery wire. FIG. 6B is a cross-sectional view of the distal delivery wire residing within a non-furrowed section of the hollow proximal delivery wire. FIG. 6C is a cross-sectional view of the distal delivery wire residing within a furrowed section of the hollow proximal delivery wire.

FIG. 7A depicts the manually adjustable central clot stabilizer in a partially-collapsed state. FIG. 7B depicts the manually adjustable central clot stabilizer in an expanded state.

DETAILED DESCRIPTION

Embodiments of the present disclosure provide for minimally invasive removal of accumulated material, such as a clot or embolism, disposed in a patient's (mammalian, including human or otherwise) vascular system. Certain embodiments of the present disclosure are particularly applicable for extraction of material in distal, narrow, tortuous segments of the neuro-blood vessels. In a general embodiment, the endovascular device of the present disclosure includes two opposing capture members that are slidably coupled to each other. Each capture member preferably comprises an open end and a tapered end, where the open end of each capture member face one another. In one embodiment, the endovascular device can be delivered to the site of the material deposit using a catheter. The capture members can be placed on each side of the material deposit with the open ends facing the material deposit. Preferably, the majority of the material deposit is moved into the capture members when the capture members progresses toward one another. In one closed configuration, the open end of the capture members meet one another to form an enclosure to capture and retain the material deposit contained therein. The capture members can be withdrawn in this closed configuration and/or be pulled into a catheter, thereby removing the material deposit.

Figure 1:
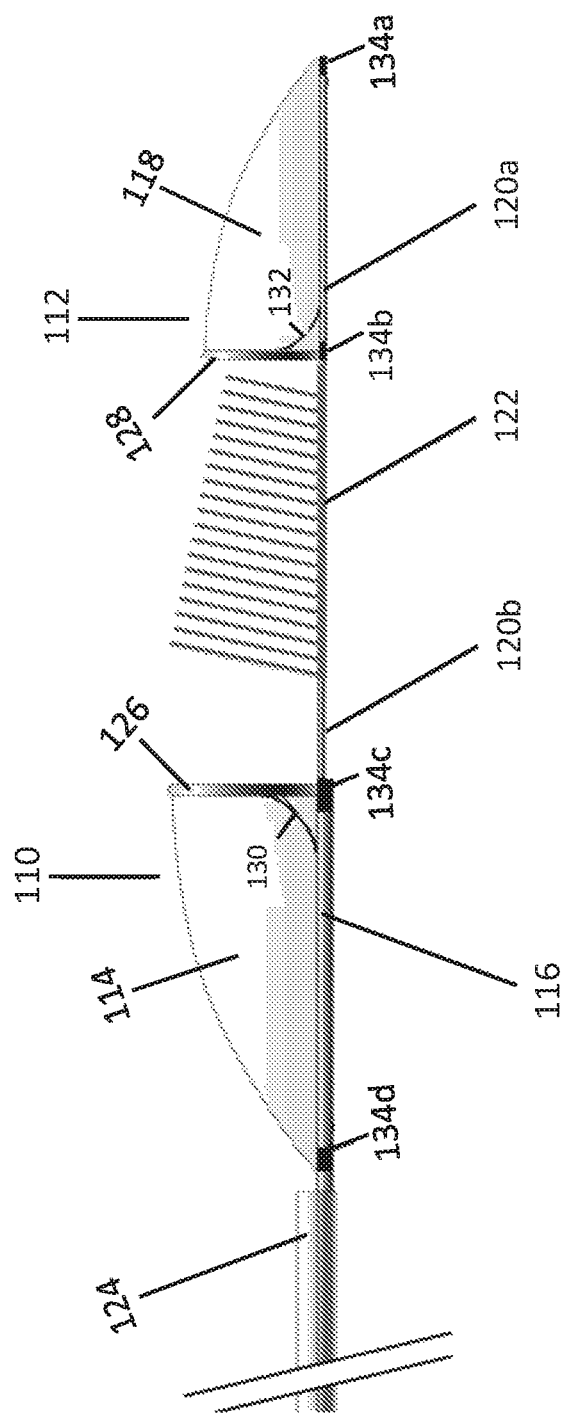
FIG. 1 is a side perspective view of a first embodiment of the clot encasement and removal system. The central clot stabilizer is in the form of a brush and is coupled to the distal capture member.
Figure 2:
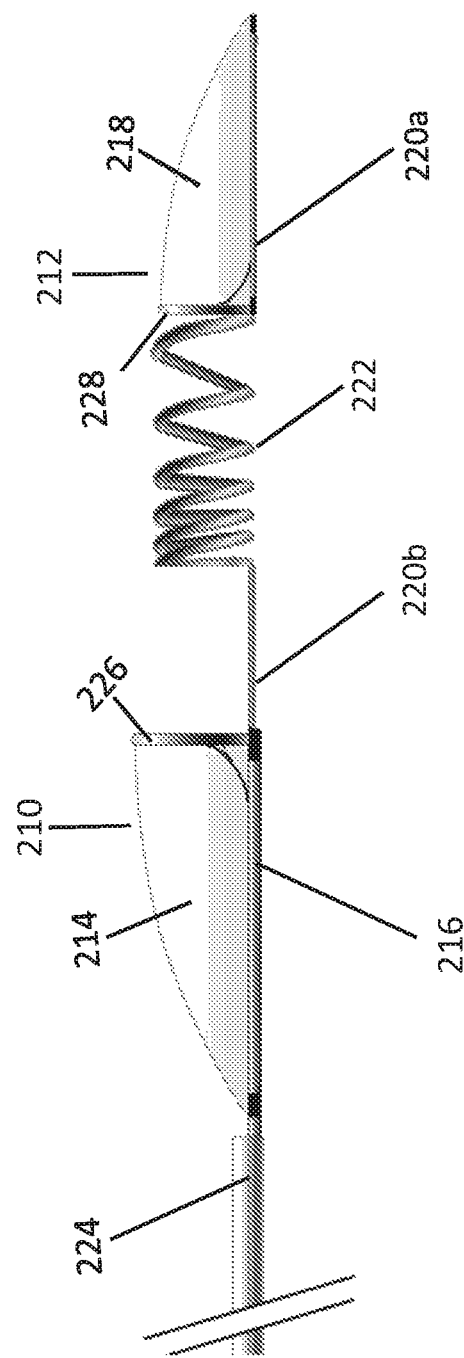
FIG. 2 is a side perspective view of a second embodiment of the clot encasement and removal system. The central clot stabilizer is in the form of a coil and is coupled to the distal capture member.
Figure 3:
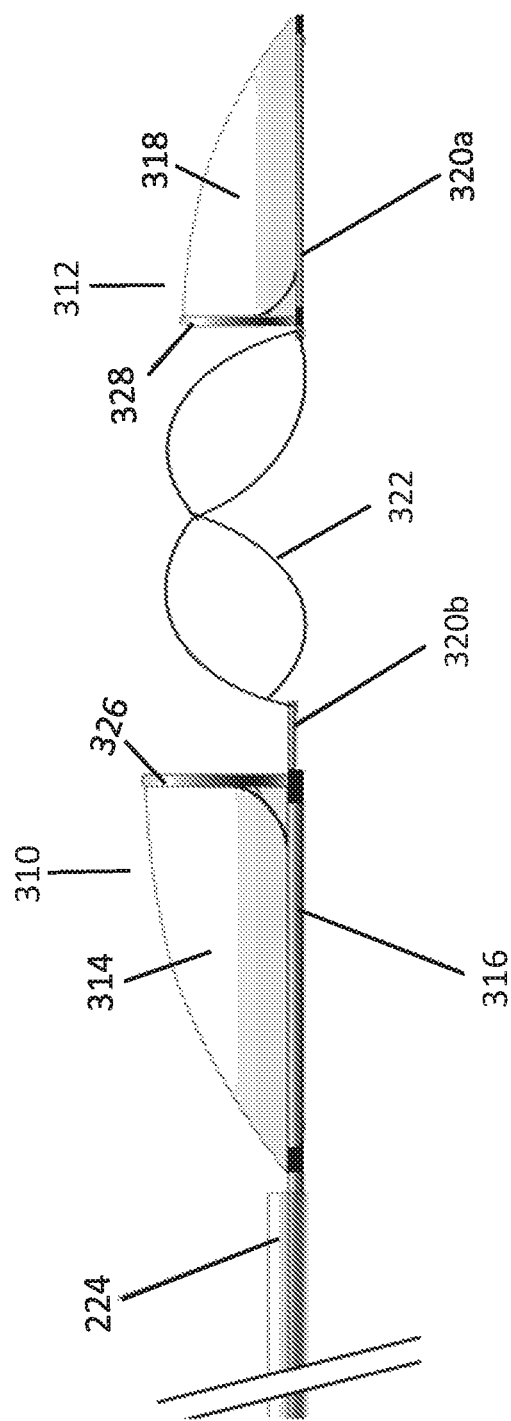
FIG. 3 is a side perspective view of a third embodiment of the clot encasement and removal system. The central clot stabilizer is in the form of a lemniscate and is coupled to the distal capture member.

FIGS. 1-6 show certain specific embodiments according to the aspects of the present invention. FIGS. 1-3 depict a side perspective view of three embodiments of the clot encasement and removal system. The three embodiments differ in the shape of the central clot stabilizer. The embodiment depicted in FIG. 1 includes a brush-like central clot stabilizer. The embodiment depicted in FIG. 2 includes a coil-shape central clot stabilizer. The embodiment depicted in FIG. 3 includes a lemniscate-shaped central clot stabilizer.

As shown in FIG. 1, the clot encasement and removal system comprises two capture members 110 and 112. Capture member 112 is the distal capture member and capture member 110 is the proximal member. The proximal and distal qualifiers describe the relative distances from a care provider (e.g., physician) who may be using the clot encasement device.

Proximal capture member 110 comprises a proximal encasement sleeve 114 and a hollow proximal delivery wire 116. Distal capture member 112 comprises a distal encasement sleeve 118 and a discontinuous delivery wire 120. The discontinuous delivery wire 120 is divided into distal segment 120a and proximal segment 120b. Distal and proximal segments of the discontinuous delivery wire 120 are bisected by a central stabilizer 122. Bisection of the discontinuous delivery wire 120 by the central stabilizer 122 does not necessarily divide distal and proximal segments of the discontinuous delivery wire 120 into two equal parts, such that the distal and proximal segments 120a and 120b may of different lengths.

At least a portion of the central stabilizer 122 comprises a cross-sectional shape that is different from the cross-sectional shape of the distal segment 120a of the discontinuous delivery wire 120. In some embodiments, the cross-sectional shape of the distal segment of the discontinuous delivery wire is circular. The cross-sectional shape of central stabilizer 122 may be constant or may vary along the length of the central stabilizer 122. The cross-sectional shape at least one point along the length of the central 122 is different from the cross-sectional shape of the distal segment 120a of the discontinuous delivery wire 120.

At least a portion of the proximal segment 120a of the discontinuous delivery wire 120 resides within the hollow proximal delivery wire 116. The inclusion of two distinct delivery wires, hollow proximal delivery wire 116 and the discontinuous delivery wire 120, allows the proximal and distal capture members to be maneuvered independently.

The proximal capture member 110 and the distal capture member 112 may also be maneuvered in unison.

Figure 5:
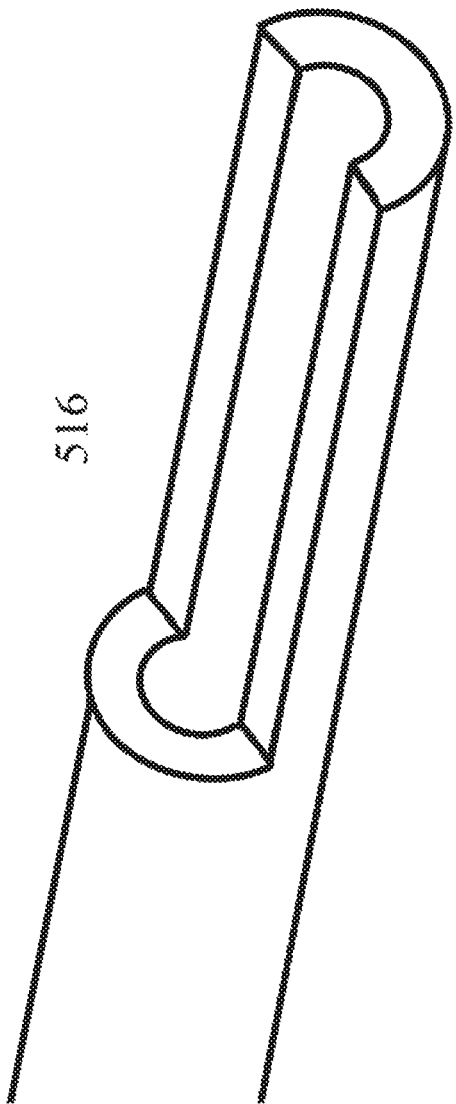
FIG. 5 is a perspective view of a hollow proximal delivery wire with a furrowed semi-cylinder. The furrow allows at least a portion the central stabilizer to be withdrawn into the proximal encasement sleeve.

As depicted in FIG. 5, the hollow proximal delivery wire 516 may comprise a furrowed semi-cylinder. The furrow allows at least a portion of the central stabilizer to be withdrawn into the proximal encasement sleeve. The length of the furrow may be selected based upon the particular application. In some embodiments, the furrow may be of a length that allows a portion of the central stabilizer to be withdrawn into the proximal encasement sleeve. In other embodiments, the furrow may be of a length that allows the entire length of the central stabilizer to be withdrawn into the proximal encasement sleeve. The furrow provides the hollow proximal delivery wire with an open section through which the central stabilizer may pass. In this fashion, the open furrowed area prevents the central stabilizer from collapsing to fit within the proximal delivery wire hollow.

The hollow proximal delivery wire 116 and discontinuous delivery wire 120 may comprise a radiopaque material. Non-limiting examples of a radiopaque material include platinum or tantalum DFT Nitinol. The radiopaque material provides a radiopaque marker that may be used to aim and maneuver different sections of the clot encasement. The embodiment depicted in FIG. 1 includes four distinct radiopaque markers which are located on the hollow proximal delivery wire 116 and discontinuous delivery wire 120. The discontinuous delivery wire 120 comprises radiopaque markers 134a and 134b. The hollow proximal delivery wire 116 comprises radiopaque markers 134c and 134d. In this embodiment, the radiopaque markers are located at open and tapered sections of proximal encasement sleeve 114 and distal encasement sleeves 118. The location and number of radiopaque markers is not limited to the location and number of radiopaque markers depicted in FIG. 1. Radiopaque markers may be located at any location on the clot encasement device. Any number of radiopaque markers may be incorporated into the clot encasement device. For example, a clot encasement device may include 0, 1, 2, 3, 4, 5, 6, or more radiopaque markers.

Proximal capture member 110 and distal capture member 112 may further comprise a frame component. The frame component may be coupled to an open end of the encasement sleeve. The frame component may be coupled to the capture member delivery wire. The frame component aids in providing rigidity for maintaining the shape and size of open ends of encasement sleeves in expanded configurations. Frame components are preferably circular in shape to match the shape of the target blood vessel. In other embodiments, however, frame components can have any shape in the expanded configuration desired, such as circular, oval, rectangular or any other regular or irregular shapes that may be suitable to the particular application. In the embodiment depicted in FIG. 1, distal frame component 128 is coupled to the open end of distal encasement sleeve 118 and to hollow proximal delivery wire 116. Proximal frame component 126 is coupled to the open end of proximal encasement sleeve 114 and to the distal segment 120a of discontinuous delivery wire 120.

The angle between a frame component and a delivery wire may be fixed or may be adjustable. Proximal capture member 110 and/or distal capture member 112 may further comprise a fastening component slidably coupled to the respective delivery wire. The fastening component allows a coupling angle of the respective frame component to be adjusted. In the embodiment depicted in FIG. 1., proximal capture member 110 comprises proximal fastening component 130, which is coupled to hollow proximal delivery wire 116 and proximal frame component 126. Distal capture member 112 comprises distal fastening component 132, which is coupled to the distal segment 120a of distal delivery wire 120 and distal frame component 128.

The size and shape of the proximal and distal frame components may be the same or different. In one embodiment, the proximal frame component 126 and distal frame component 128 are both circular in shape. The diameter of proximal frame component 126 is different from the diameter of distal frame component 128. The diameters (or other size for a non-circular frame) of the proximal and distal frame components may be selected such that one frame component fits within the other frame component. This allows the frame components, and the encasement sleeves to which they are coupled, to fit within one another, thereby providing an encasement volume within which an obstruction may be captured. The sized of the proximal and distal frame components may be selected to provide a tight junction between open ends of respective capture members.

Frame components preferably comprises a superelastic and/or self-expanding material. In particular, the superelastic and/or self-expanding material preferably have properties that allow it to have a deformed shape under one condition and to recover its original shape prior to deformation, which can also be referred to as an expanded configuration, in response to exposure to an activation mechanism. Preferably, the material can include a memory-shaped heated alloy such as nitinol, or nickel titanium, which is a metal alloy of nickel and titanium. Nitinol alloys exhibit two closely related and unique properties: shape memory and superelasticity. Shape memory refers to the ability of nitinol to undergo deformation at one temperature, then recover its original, un-deformed shape upon heating above its "transformation temperature." That is, nitinol alloy has a biased expanded condition and may be compressed into a collapsed or deformed condition before use. During use, it may be exposed to temperature above the transformation threshold, thereby causing it to revert back to its un-deformed and/or original shape. Frame components can also comprise any flexible and/or elastic material that allows frame components to be compressed, or deformed by a radial force, to fit into a catheter, such as catheter 124 shown in FIG. 1, without sustaining any damage and revert back to its original shape once released from the catheter.

In one embodiment, the diameter of frame components 126 and 128 ranges between about 10 microns to 500 microns. In a preferred embodiment, the diameter of frame components 126 and 128 ranges between about 80 microns to about 120 microns. In another preferred embodiment, the diameter of frame components 126 and 128 ranges between about 95 microns to about 105 microns.

The diameter of at least one of frame components 126 and 128 in the expanded configuration, and capture member open ends, is preferably configured to substantially match the diameter of the particular lumen or blood vessel of interest in which the target material deposit, e.g., clot, is disposed. In such an expanded configuration, frame components 126 and/or 128 preferably contact the inner wall of the target blood vessel gently, e.g., without exerting significant force that can damage the blood vessel. This allows at least one capture member 110 or 112 to extend across the interior, or lumen, of the blood vessel where effectively most or all the fluid and material flowing through the target blood vessel are directed through the respective extended capture member 110 or 112. In one embodiment, the diameter of at least one encasement sleeve open end is in a range of about 1.5 mm to about 6 mm, and preferably in a range of about 2 mm to about 4.5 mm. In another preferred embodiment, the diameter of at least one encasement sleeve open end is between about 2.5 mm and about 3 mm.

The clot encasement device comprises a central stabilizer. In some embodiments, the central stabilizer comprises a self-expanding material configured to have a collapsed configuration and an expanded configuration. The central stabilizer functions to provide one or more points of contact with an obstruction, e.g., a clot. Contacting an obstruction with the central stabilizer allows the central stabilizer to exert a stabilizing force on the obstruction. Obstruction stabilization is especially useful for long clots (>5 mm). The central stabilizer/obstruction contact may occur at either end of the obstruction, between ends of the obstruction, or along the entire length of the obstruction. Contacting an obstruction with the central stabilizer allows the obstruction to be stabilized, or held in place. The obstruction may be stabilized by the central stabilizer while moving one or both capture members over the obstruction surface to encapsulate the obstruction without significant compression and/or deformation. Contacting an obstruction with the central stabilizer may be used to apply a dragging force uniformly at one or more points along the length of the obstruction. In this fashion, the central stabilizer may be used to effectively manipulate the obstruction at least partially inside one or both capture members. Manipulation of an obstruction may be accomplished without significant compression and deformation of the clot.

Figure 7B:
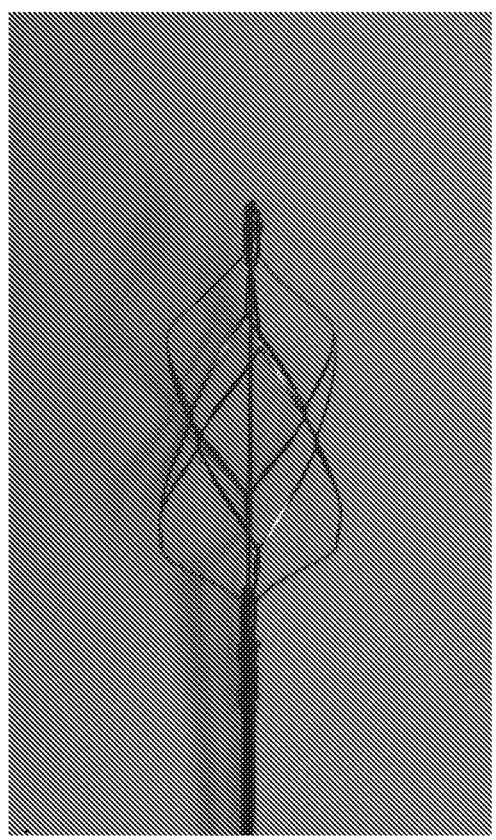
FIGS. 7A-7B depict one embodiment of the clot encasement and removal system wherein the central clot stabilizer is manually adjustable.
Figure 7A:
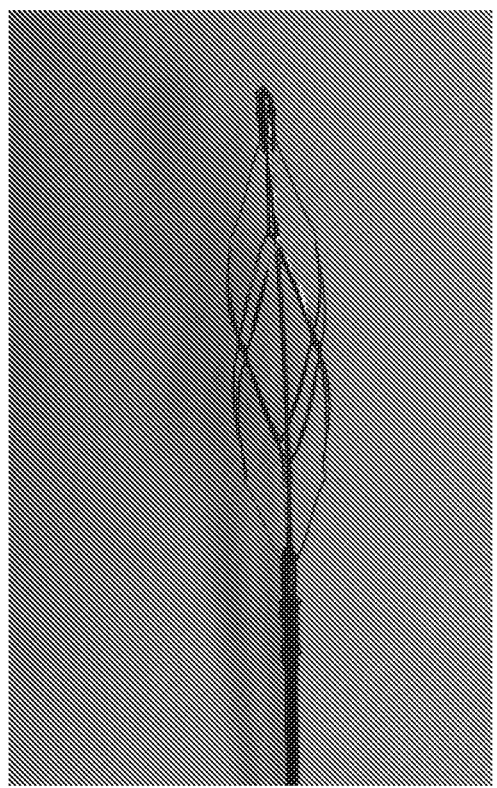

In further embodiments, the central stabilizer is manually adjustable. Manual adjustment of the central stabilizer allows the user to control the central stabilizer expansion state. The central stabilizer may reside within the hollow proximal delivery wire in a fully or partially collapsed state. Upon being directed or manipulated out of the hollow proximal delivery wire, the central stabilizer may remain in a fully collapsed state. The central stabilizer may include one or more radiopaque markers to assist in delivery and placement of the central stabilizer relative to an obstruction. The expansion state of the central stabilizer may be manually adjusted from fully collapsed to fully expanded, or any expansion state therebetween. FIG. 7A depicts the manually adjustable central clot stabilizer in a partially-collapsed or partially-expanded state. FIG. 7B depicts the manually adjustable central clot stabilizer in an expanded state. The expansion state of the central clot stabilizer may be selected and adjusted to optimally position, grasp, prod, penetrate, pierce, nudge, envelop, clasp, and/or retrieve an obstruction.

The central stabilizer 122 may be at least partially withdrawn into the proximal encasement sleeve. The hollow proximal delivery wire may comprise a furrow whose shape and size are selected to allow at least a portion of the central stabilizer to overlap at least a portion of the length of the hollow proximal delivery wire 116. In this fashion, the central stabilizer may be withdrawn into the proximal encasement sleeve. The central stabilizer 122 may be provided with or have incorporated within it a radiopaque material. The central stabilizer 122 may comprise one or more radiopaque markers.

The size and shape of the central stabilizer may be selected depending on the blood vessel and obstruction. The central stabilizer size may be selected such that a portion of, or the entirety of the central stabilizer fits within at least one encasement sleeve. The orthogonal size of the central stabilizer may range from about 1 to about 6 mm, and preferably from about 2 mm to about 3 mm. The orthogonal size refers to the dimension of the central stabilizer that is orthogonal to the line created by the delivery wires. The length of the central stabilizer may range between about 5 mm to about 40 mm, and preferably from about 10 mm to about 20 mm. The central stabilizer may comprise a superelastic and/or self-expanding material. In particular, the superelastic and/or self-expanding material preferably have properties that allow it to have a deformed shape under one condition and to recover its original shape prior to deformation, which can also be referred to as an expanded configuration, in response to exposure to an activation mechanism. The central stabilizer material can include a memory-shaped metal or alloy such as nitinol, or nickel titanium, which is a metal alloy of nickel and titanium. In some embodiments, the central stabilizer may be made of a polymer. In further embodiments, the central stabilizer is made of a combination of a polymer and a memory-shaped metal or alloy.

The central stabilizer is provided in a shape that is different from the delivery wire shape. In some embodiments, the cross-sectional shape of at least a portion of the central stabilizer is different from a cross-sectional shape of the distal segment of the discontinuous delivery wire. A discontinuous delivery wire cross-sectional shape may be square, round, oval, rectangular, etc. The central stabilizer is shaped such that at least a portion of the central stabilizer's cross-sectional shape is different from the discontinuous delivery wire cross-sectional shape. In comparison to the delivery wire, the central stabilizer shape provides a different or additional surface area for engaging an obstruction. The central stabilizer shape may be a helix, a double helix, a lemniscate, a coil or spring, or a brush with projections emanating from a base. A helix, double helix, or coil or spring may have ring coils with the same or different diameters. The ring coil diameters may be constant along the central stabilizer length or they may be variable. The ring coil diameters may increase or taper in size. The ring coil diameters may be of alternating diameters. The helix, spring, or coil may be wound clockwise or counterclockwise. The coil pitch may be tight, for example, 0.5 mm. The coil pitch may be intermediate, for example 1 mm to 2 mm. The coil pitch may be loose, for example 3 mm and above. The coil pitch may vary from about 0.5 mm to about 5 mm. The coil rings may be touching or they may be separated. A double helix may comprise two component helices with the same or different dimensions. In some embodiments, a central stabilizer comprises a plurality of component wires. In some embodiments, a central stabilizer comprises a braided shape, for example, a bi-axial or higher-order braid. In central stabilizer embodiments comprising a plurality of component wires, the wires may be separate from each other or may be attached to each other at one or more points. In a brush-shaped central stabilizer, the projections may be of uniform length or of varying length. The distance between the projections may be constant or may vary. In some embodiments, the distance between projections varies from about 0.5 mm to about 3 mm. The projection angle may vary from acute to obtuse. In a preferred embodiment, the projection angle is 90 degrees. In some embodiments, a central stabilizer may comprise a combination of different shapes.

The distal and proximal encasement sleeves may be formed of any material which is flexible and compatible with bodily fluids such as blood. Non-limiting examples of suitable materials include polymeric film materials, such as, but not limited to, polyurethane, polyolefin, polyester, and silicone polymers. In an embodiment using such polymeric film material, distal and/or proximal encasement sleeve tapered ends can further include apertures of sufficient size to allow fluids to flow through distal and/or proximal encasement sleeve while retaining the captured material deposit. In some embodiments, distal and/or proximal encasement sleeves comprise a polymeric net-like material having a plurality of apertures throughout the material, such as, but not limited to, a woven mesh of polymeric material, metal, and/or other superelastic, self-expanding, and/or memory shape alloy such as nitinol. In certain embodiments, the woven mesh can comprise a combination of polymers, metals, and/or metal alloys. While the figures may depict body members formed of a film material, it is intended to be exemplary and not limiting, as it is understood that such body members can be made of net-like material without departing from certain aspects of the present invention. In one embodiment, the material of distal and/or proximal encasement sleeve can comprise material similar to that of the material of frame component, providing it a biased shape in the expanded configuration that allows distal and/or proximal encasement sleeve to remain open as it extends away from its respective frame component. In some embodiments, the total length of distal and proximal encasement sleeves is between about 5 mm and about 30 mm. In a preferred embodiment, the total length of both distal and proximal encasement sleeves is between about 8 mm and about 20. In another preferred embodiment, the total length of distal and proximal encasement sleeves is between about 10 mm and 12 mm. In yet another preferred embodiment, the total length of distal and proximal encasement sleeves is about 10 mm.

In one embodiment, a user can hold hollow proximal delivery wire 116 static, thereby keeping proximal capture member 110 in one position, while pushing or pulling distal guide member 120 to adjust the position of distal capture member 112. In another embodiment, the user can hold distal guide member 120 constant, thereby keeping distal capture member 112 in one position, while pushing or pulling hollow proximal delivery wire 116 to adjust the position of proximal capture member 110. In yet another embodiment, both delivery wires 116 and 120 can be adjusted at the same time to achieve the desired positions of capture members 110 and 112 and central stabilizer 122.

The body of either delivery wire 116 or 118 preferably has a length sufficient to extend through the vascular system of a patient to reach the target accumulation and place endovascular device in the desired deployment location. In one embodiment, either delivery wire 116 or 118 has a length of between about 50 cm and about 250 cm, more preferably a length of about 125 cm and about 175 cm. The diameter of either delivery wire 116 or 118 may be constant or may vary along the length of the respective delivery wire 116 or 118. For example, the diameter of one guide member toward the proximal end away from the user may be between about 0.2 mm and about 1 mm, and preferably about 0.3 mm and about 0.4 mm, while the diameter near the distal end near the clot may be between about 0.05 mm and about 1 mm, and more preferably about 0.1 mm and about 0.2 mm. Accordingly, the diameter of either guide member 116, 118 may taper from the proximal end to the distal end.

Figure 4:
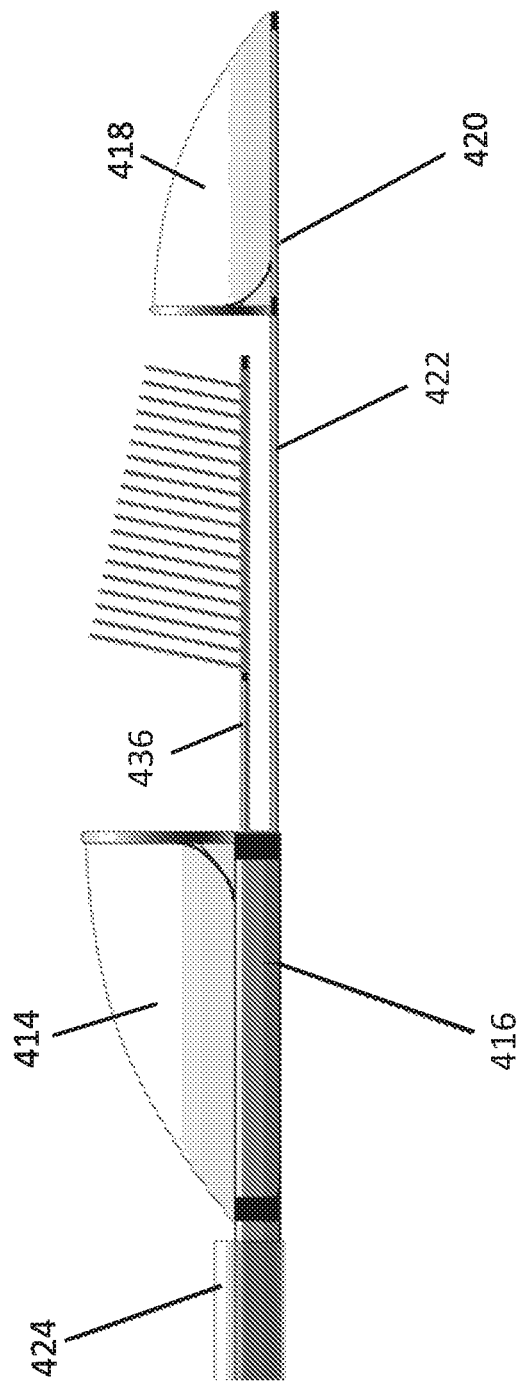
FIG. 4 is a side perspective view of a fourth embodiment of the clot encasement and removal system. The central clot stabilizer is in the form of a brush. The central clot stabilizer and distal capture member are coupled to distinct delivery wires.

Referring to FIG. 4, some embodiments of a clot encasement device may comprise a proximal capture member coupled to a hollow proximal delivery wire, a central stabilizer coupled to a central delivery wire and a distal capture member coupled to a distal delivery wire. The central and distal delivery wires are distinct wires which allow independent control of the respective central stabilizer and distal capture member. At least a portion of the central and distal delivery wires reside within the hollow proximal delivery wire, and are controlled by manipulation through the interior of the hollow proximal delivery wire. Each of the proximal, central, and distal delivery wires may comprise at least one radiopaque marker. The radiopaque marker enables visualization of the respective delivery wire to which the marker is coupled. The proximal, central, and distal delivery wires may be independently controlled for independent manipulation of the respective proximal capture member, central stabilizer, and distal capture member.

Although the embodiments of the present disclosure and their advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the present disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

The invention claimed is:

1. A device for removing an obstruction in a lumen comprising:
   a proximal capture member; and
   a distal capture member;
   wherein the proximal capture member comprises a proximal encasement sleeve and a hollow proximal delivery wire;
   wherein the distal capture member comprises a distal encasement sleeve and a discontinuous delivery wire;
   a central stabilizer bisecting the discontinuous delivery wire into proximal and distal segments;
   wherein a cross-sectional shape of at least a portion of the central stabilizer is different from a cross-sectional shape of the distal segment of the discontinuous delivery wire; and
   wherein at least a portion of the proximal segment of the discontinuous delivery wire lies within the hollow proximal delivery wire,
   wherein at least a portion of the proximal hollow delivery wire comprises a furrowed semi-cylinder that allows at least a portion the central stabilizer to be withdrawn into the proximal encasement sleeve.

2. The device of claim 1, wherein each of the proximal and distal capture members further comprises an open end and a tapered end, a frame component coupled to the respective encasement sleeves of the proximal and distal capture members, said encasement sleeves extending between said open end and said tapered end.

3. The device of claim 2, wherein said proximal frame component and distal frame component comprise a self-expanding material configured to have a collapsed configuration and an expanded configuration.

4. The device of claim 3, wherein the device further comprises a catheter.

5. The device of claim 4, wherein collapsed configurations of the proximal capture member, distal capture member, and central stabilizer reside within the catheter.

6. The device of claim 2, wherein the central stabilizer comprises a self-expanding material configured to have a collapsed configuration and an expanded configuration.

7. The device of claim 2, wherein the central stabilizer is manually adjustable.

8. The device of claim 7, wherein an expansion state of the manually adjustable central stabilizer comprises a fully collapsed state, a fully expanded state, or any expansion state therebetween.

9. The device of claim 2, wherein at least one of the proximal or distal capture members further comprises a fastening component slidably coupled to the respective delivery wire, allowing a coupling angle of the respective frame component to be adjusted.

10. The device of claim 2, wherein the proximal and distal encasement sleeves are devoid of any fenestrations.

11. The device of claim 2, wherein the proximal and distal encasement sleeves comprise a woven material of at least one of the following: a polymer, a metal, and any combination thereof.

12. The device of claim 2, wherein the proximal and distal encasement sleeves comprise a soft and flexible material.

13. The device of claim 2, wherein the proximal and distal encasement sleeves comprise a self-expanding material configured to bias the encasement sleeve into an expanded configuration.

14. The device of claim 2, wherein each of the proximal and distal encasement sleeves covers at least a portion of a surface of the frame component to which it is coupled.

15. The device of claim 2, wherein at least one of the proximal frame component, the distal frame component, or the central stabilizer is configured to deliver a therapeutic substance to said obstruction.

16. The device of claim 2, wherein a proximal frame component diameter is different from a distal frame component diameter.

17. The device of claim 2, wherein each of the proximal and distal encasement sleeves covers at least a portion of a surface of the frame component to which it is coupled.

18. The device of claim 2, wherein at least one of the proximal frame component, the distal frame component, or the central stabilizer is configured to deliver a therapeutic substance to said obstruction.

19. The device of claim 1, wherein at least one of the proximal or distal capture members further comprises a support arm.

20. The device of claim 19, wherein the support arm is coupled to the respective delivery wire and the respective frame component.

21. The device of claim 1, further comprising a radiopaque marker.

22. The device of claim 1, further comprising a radiopaque marker.

23. A device for remove an obstruction in a lumen comprising:
    a proximal capture member; and
    a distal capture member;
    wherein the proximal capture member comprises a proximal encasement sleeve and a hollow proximal delivery wire;
    wherein the distal capture member comprises a distal encasement sleeve and a discontinuous delivery wire;
    a central stabilizer bisecting the discontinuous delivery wire into proximal and distal segments;
    wherein a cross-sectional shape of at least a portion of the central stabilizer is different from a cross-sectional shape of the distal segment of the discontinuous delivery wire; and
    wherein at least a portion of the proximal segment of the discontinuous delivery wire lies within the hollow proximal delivery wire,
    wherein at least a portion of the proximal hollow delivery wire comprises a furrowed semi-cylinder that allows at least a portion the central stabilizer to be withdrawn into the proximal encasement sleeve,
    wherein the furrowed semi-cylinder comprises a length that is equal to or greater than a central stabilizer length to allow the entire length of the central stabilizer to reside within the proximal encasement sleeve.

* * * * *